United States Patent [19]
Ramon et al.

[11] Patent Number: 5,368,362
[45] Date of Patent: Nov. 29, 1994

[54] SEATING APPARATUS FOR SUPPORTING A PERSON IN A MANNER WHICH REDUCES SEDENTARY AILMENTS BY ALLOWING FOR A TILTING MOVEMENT OF THE SEATING MEANS

[76] Inventors: Arie Ramon, Mishol Hahadas 11, Ramot 2; Elath Almagor, Ramot 37, both of Jerusalem, Israel

[21] Appl. No.: 839,421

[22] Filed: Feb. 20, 1992

[30] Foreign Application Priority Data

Feb. 26, 1991 [IL] Israel ................................. 97364

[51] Int. Cl.⁵ ................................................ A47C 3/00
[52] U.S. Cl. ............................. 297/310; 297/258; 297/272; 297/464; 248/188.7
[58] Field of Search ............. 297/310, 468, 258, 278, 297/487, 488, 4, 272, 464; 248/188.7

[56] References Cited

U.S. PATENT DOCUMENTS

| | | | |
|---|---|---|---|
| 2,049,539 | 8/1936 | Greenwood | 297/258 |
| 3,145,053 | 8/1964 | Thompson | 297/488 |
| 3,409,326 | 11/1968 | Kerner | 297/488 |
| 4,084,273 | 4/1978 | Haynes | 297/258 |
| 4,183,579 | 1/1980 | Gonzalez | 297/310 |
| 4,813,746 | 3/1989 | Mulholland | 297/464 |
| 4,828,208 | 5/1989 | Peterson | 248/188.7 |

FOREIGN PATENT DOCUMENTS

| | | | |
|---|---|---|---|
| 561720 | 11/1957 | Belgium | 297/258 |
| 48348 | 1/1889 | Germany | 297/258 |
| 3201335 | 7/1983 | Germany | 297/310 |
| 3207941 | 9/1983 | Germany | 297/310 |
| 3605362 | 8/1987 | Germany | 297/258 |

*Primary Examiner*—Flemming Saether

[57] ABSTRACT

A seating apparatus is disclosed for supporting a person in a manner which reduces sedentary ailments by allowing for a free tilting movement of the seat of the apparatus. The seating apparatus includes a seat which has a single leg which rises from a leg pad. Two rollers or castors are connected to the structure supporting the single leg. The single leg has a convexly-shaped underside which allows for the tilting movement. The curvature of the radius of the convexly-shaped underside of the single leg is preferably from 25–70 cm.

6 Claims, 5 Drawing Sheets

SEATING APPARATUS FOR SUPPORTING A PERSON IN A MANNER WHICH REDUCES SEDENTARY AILMENTS BY ALLOWING FOR A TILTING MOVEMENT OF THE SEATING MEANS

BACKGROUND OF THE INVENTION

1. Technical Field of the Invention

The present invention relates to a support for a person who assumes a sitting or quasi-sitting position.

2. Description of the Prior Art

There are devices presently known to the art for supporting the body of a person who attends to certain functions or occupations which, while permitting more or less free movement, obligates the person sitting to assume body positions of one kind or another during certain periods of time.

Known supports mainly comprise a single supporting leg. Examples of such supports are disclosed in U.S. Pat. No. 1,417,250, to Kelly which describes a supporting device for workers who have to assume a bending or stooping position during most of their working time. The device disclosed in this reference consists mainly of a breast plate to be strapped to the body of a worker by shoulder straps with the breast plate being carried on a single supporting leg. A person using the device would be bent over and would be supported by the device on whose breast plate her or his breast region would rest while the single leg stands on the ground.

U.S. Pat. No. 3,306,658, describes a device for use by dentists or dental surgeons who, as is known, work on a person who reclines in a special chair. The dentist is supported on a saddle-like seat which rests on a single leg. This device allows almost unlimited movement to the user who is supported on her or his legs, since the person's feet remain on the ground beside the chair in which the patient reclines.

U.S. Pat. No. 4,451,080 describes a device for use by paraplegics or those or lack legs. The person sits on, and is secured to, a seat resting on a single leg and "walks" with the aid of crutches. To permit lateral movement, the single leg has, at its lower end, a pad whose downward facing surface is curved.

SHORT STATEMENT OF ADVANTAGES OF INVENTION

In comparison to the other above-mentioned devices, the present invention is intended for much wider use.

Maximum freedom of movement and agility is generally associated with the standing posture which, however, has the disadvantage of being tiring to those working. The sitting position gives more comfort, but severely limits the freedom of movement.

The present invention relates to seating means which permits the user a greater freedom of movement to a degree which allows more convenient attendance to which, which is conventionally performed by normal persons in a sitting position.

The suggested means permits a person to assume a posture closer to a standing position, as far as freedom of movement is concerned, and yet supports a major part of the body weight by the buttocks.

The claimed seating apparatus, according to experimental tests and opinion of anatomical experts, is preferable from the points of assuming a healthful, natural posture and enabling frequent small changes in sitting position to the conventional sitting position where the rump region occupies a seat and the upper part of the body is supported by a back rest against which the sitter leans with very little movement.

SUMMARY OF THE INVENTION

According to the invention, the claimed setting apparatus comprises a seat part which is supported on a single leg having a leg pad with convex, preferably spherical, underside face. At the lower part of said single leg, a supporting structure is provided, which is connected to two rollers or castors at the rear end of said structure.

In a further embodiment of the invention, the length of the single leg, and consequently the level at which the seat is held, is controllable by making the leg of two hollow cylindrical parts, one displaceable within the other, in a telescoping manner.

In comparison with other known one leg support seating devices, the present invention has a distinctly different approach to the relation between the center of curvature of the pad of the leg and the location of the center of gravity of the sitting person.

The known devices adopt one of the following two approaches:

a) small radius of curvature and center of gravity of the seater much higher than the center of curvature; or, b) large radius of curvature and the center of gravity of the seater below the center of curvature to create a torque which tends to bring the chair back to a certain neutral position and preventing the seater from exceeding comfortable and safe angles of incline of the chair.

Experience has shown that the preferred radius of curvature is within 25–70 cm.

The present invention intends, within the limits of practical constraints, to have the center of gravity of the seater (the seater and chair combined to be precise) to coincide with the center of curvature of the leg pad.

This configuration has the advantage of free movement with minimum strain in the back muscle and stress on the spine.

The disadvantage is that a separate mechanism to prevent exceeding safe angles of chair incline is required.

Limiting legs provide such safety.

These and further features of the invention will become clear from the following description, which refers to the accompanying drawings.

BRIEF DESCRIPTION OF THE DRAWING FIGURES

In the drawing, wherein similar reference numerals denote similar features throughout the several views.

DETAILED DESCRIPTION OF THE DRAWING FIGURES AND PREFERRED EMBODIMENTS

Figure 1:
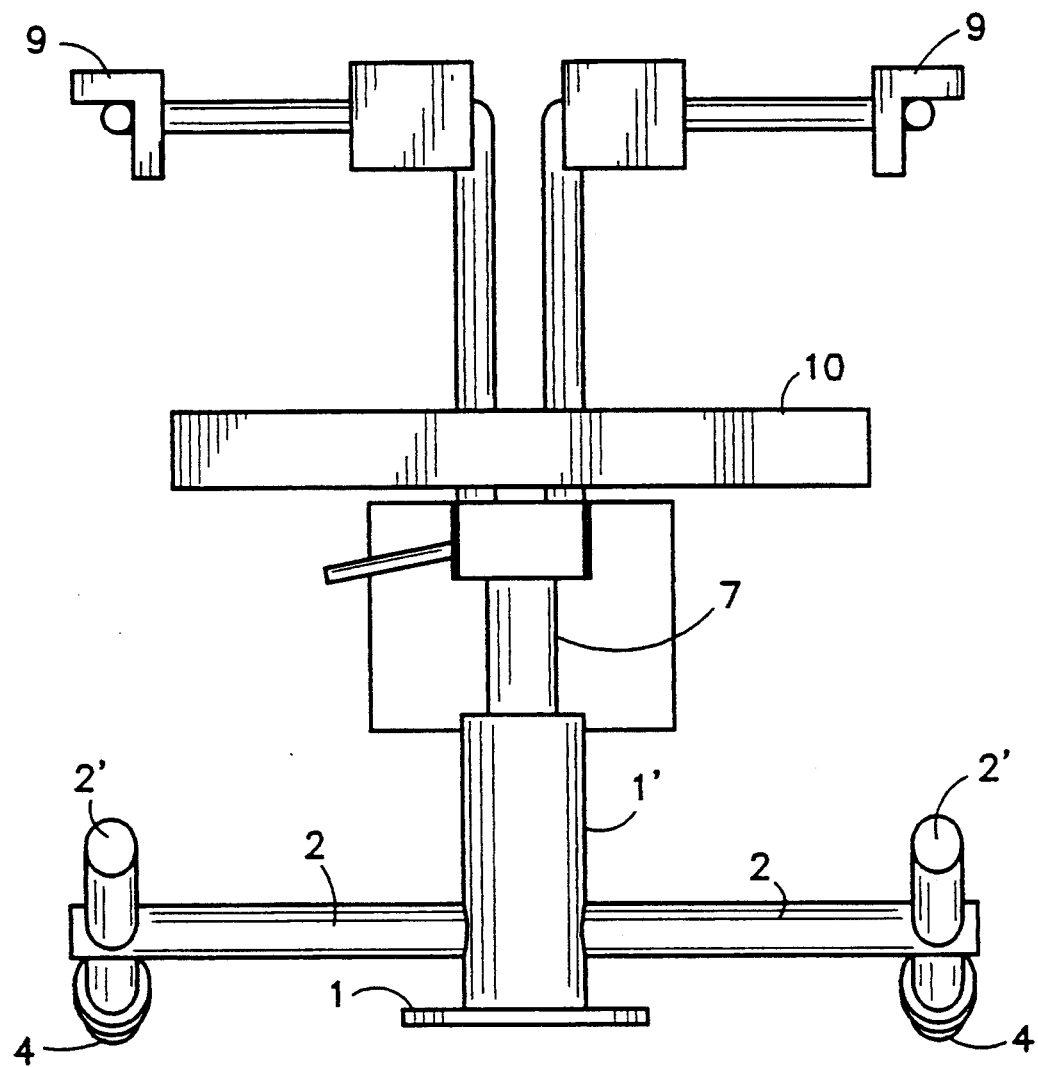
FIG. 1 is a front, elevational view of an embodiment of the seating apparatus of the present invention.
Figure 2:
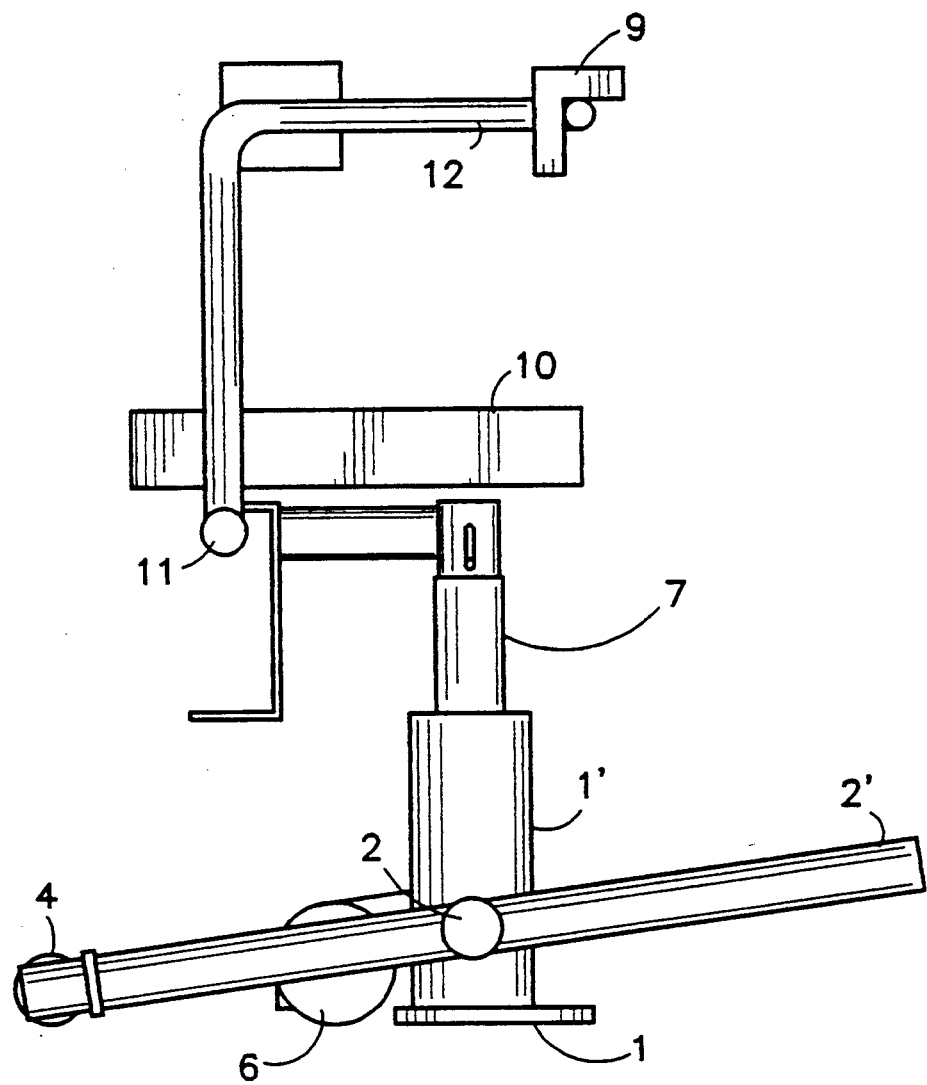
FIG. 2 is a lateral view of an alternative embodiment of the seating apparatus shown in FIG. 1.
Figure 3:
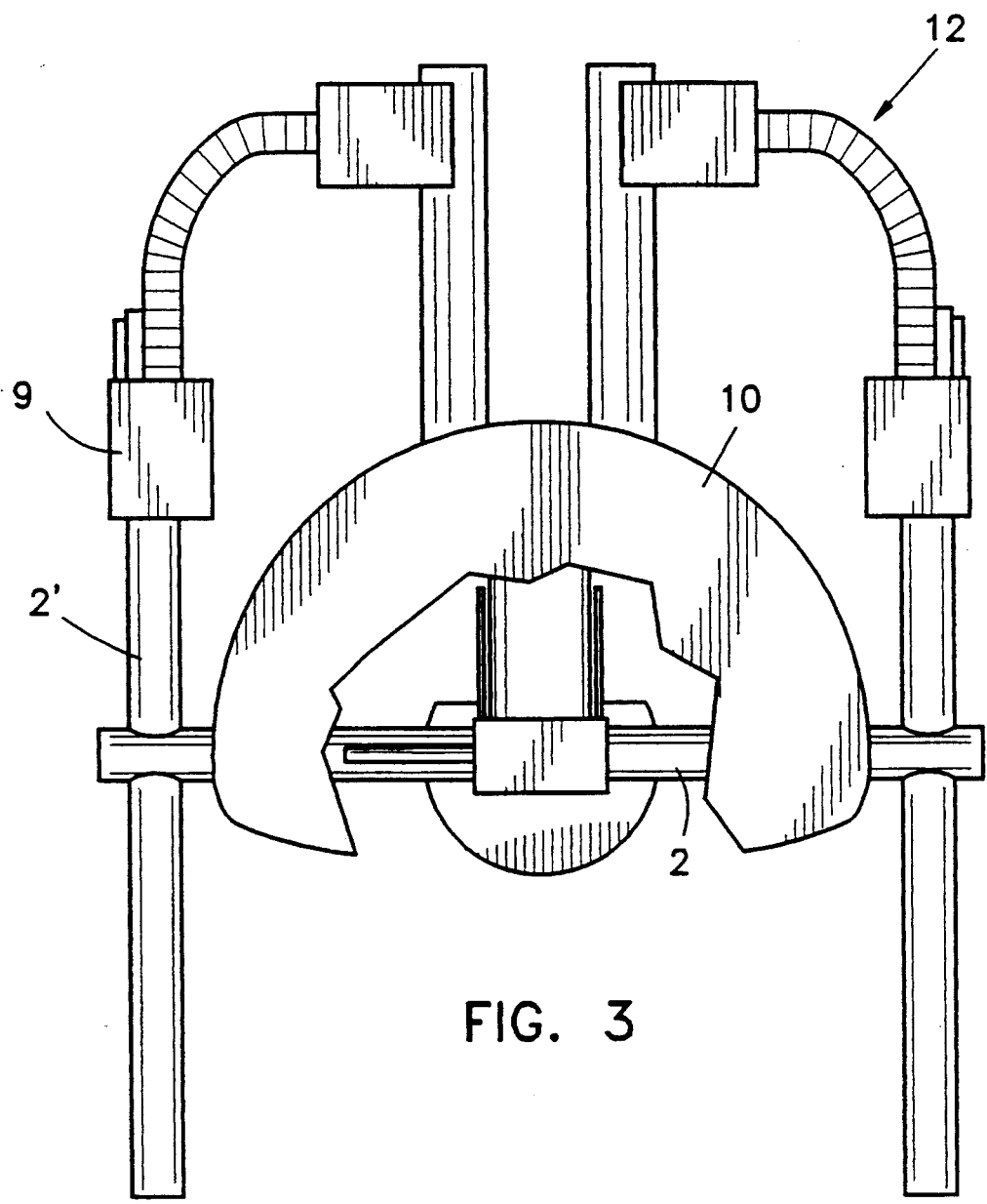
FIG. 3 is a top view of the embodiment, of the seating apparatus shown in FIG. 2.

Turning, first, to FIG. 1, a two-part single leg 1' (the two parts telescoping into one another) extends from a foot pad 1. Foot pad 1 has a convexly-curved underside. Beam 2 extends horizontally from both sides of leg part 1', to which is connected another beam 2' at right angles. To the rear end of beam 2' is affixed a roller or castor 4. A larger wheel 6 is affixed to foot beam 2' near foot pad 1. The upper part 7 of the leg (which is slidable in the lower base part 1' thereof) carries seat 10. Slightly below the seat 10, affixed to leg part 7, extends a cross beam 11 which carries arm rests 9.

A person can occupy the seat 10 facing in the direction of an abdomen support 12 comprising two halves of a body belt. When the two halves of the belt are buckled or connected together, the person on seat 10 leans on his or her belly portion onto the closed belt. When sitting on seat 10 with chair upright, the person's feet just touch the ground without loading the weight of the body onto that person's legs. When the chair is inclined by the user, an increasing, though a minor, proportion of the user's weight is transferred to the user's legs.

Figure 4:
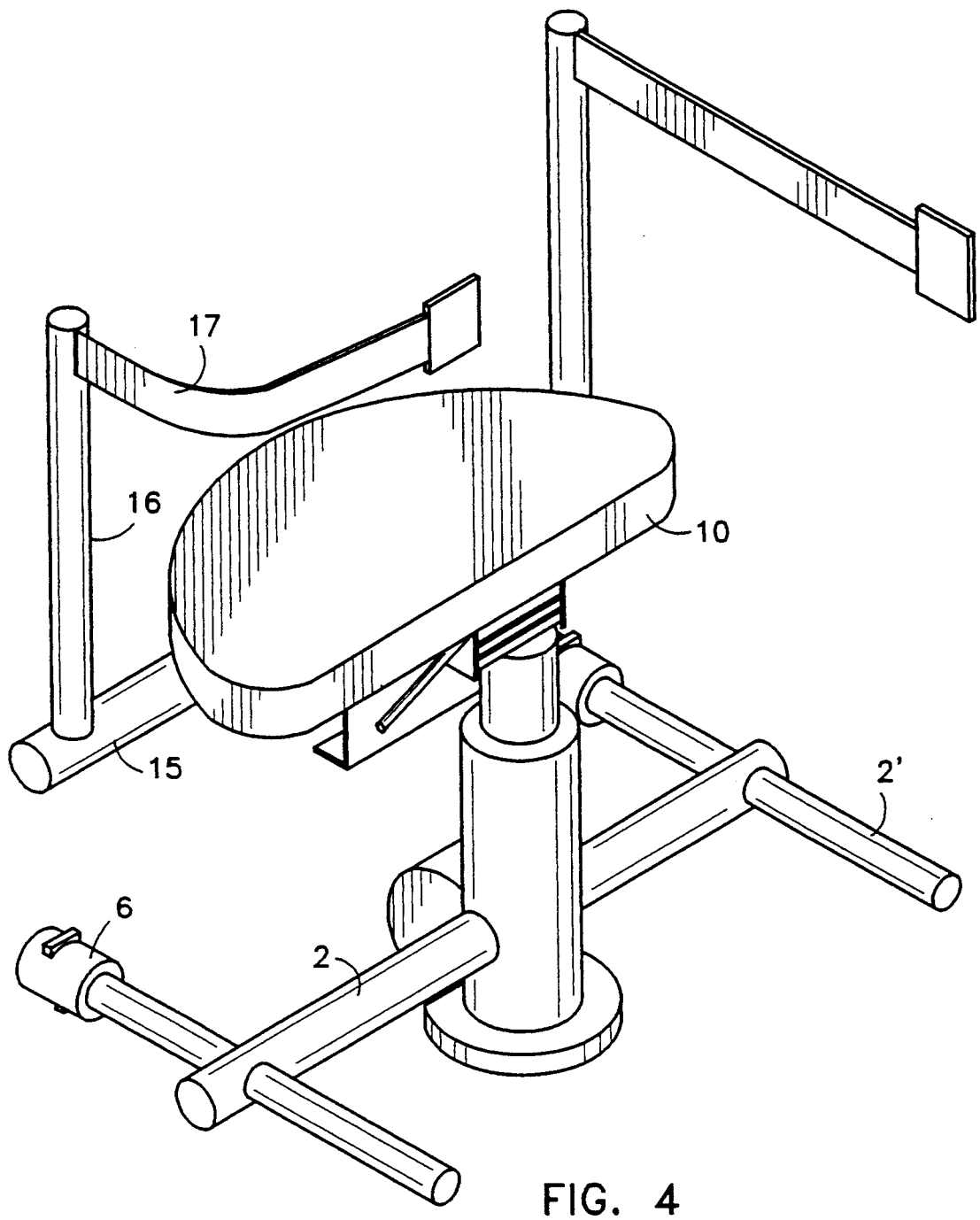
FIG. 4 is a prospective view of a further embodiment of the invention having a further abdomen supporting means; and, FIG. 5 is a prospective view of an alternative embodiment of the invention having an alternative abdomen supporting means.
Figure 5:
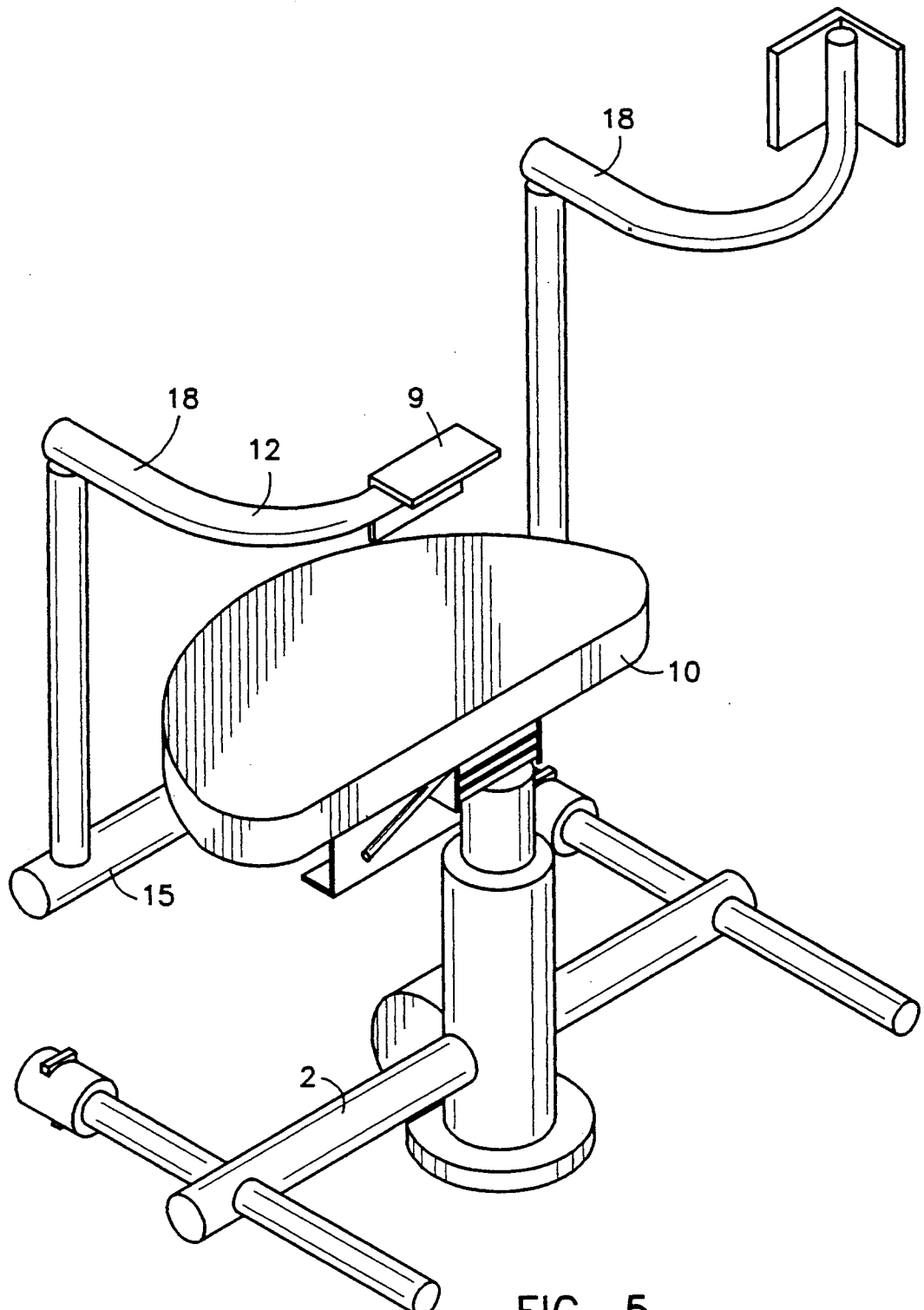

Two, further, alternative embodiments for supporting the user's abdomen are shown in FIGS. 4 and 5, respectively. In these arrangements, there extend below seat 10 substantially across the middle thereof, two arms 15 which each carry an upright 16. Uprights 16 each carry a bow-shaped member 17, which extends in a horizontal plane above seat 10. Bows 17 may be positioned at either the front or the rear of the seat apparatus and a person can lean against the bows 17 either with her or his abdomen or back.

Bows 17, as shown in the embodiment of FIG. 4, are bendable around either the user's abdomen or back. Bows, as shown in the embodiment of FIG. 5 are also positionable around either the user's abdomen or back. In FIG. 5, it is possible to swivel bows 17 at pivot 18 by pivoting the bows in an upright manner by 90°, thereby enabling the rising or seating task of a person in the seating apparatus of the invention.

Optionally, arms 15 in the embodiments of both FIGS. 4 and 5 can be meshed through gears so that symmetrical motion is caused by movement of one of the arms.

"Overtilting" is prevented by beam 2, either by castors 4 or the skived end of the beam, possibly assisted by stops at the center of the beam. When the single leg is strictly vertical, the two castors 4 are off the ground and the whole chair is support on pad 1 and the larger wheel 6. Whenever the person on seat 10 leans in the rearward direction, the front end of beam 2 rises with pad 1, which is no longer in contact with the floor, and castors 4 come down to the ground.

It will be seen that the person occupying the chair is safely sitting and can freely move his or her backside within a rough oval area of more than 10 by 10 cm and can rotate his or her body with no limitation at all. At the same time, his or her arms are entirely free to do whatever work or task that is required. The posture assumed in the chair is natural and might relieve back aches.

We claim:

1. Seating apparatus for supporting a person, comprising:
   a seat for a person to be seated in;
   a single leg for supporting said seat, said single leg having a convex-shaped underface and a central wheel along-side said convex-shaped underface; and
   a support for preventing said seat from overturning, yet allowing freedom of movement of said single leg on said convex-shaped underface and on said central wheel.

2. The seating apparatus for supporting a person according to claim 1, wherein said single leg is made of a plurality of segments which are able to be telescoped one into another.

3. The seating apparatus for supporting a person according to claim 1, further comprising means for supporting the abdomen region of the person occupying said seat, said means for supporting said abdomen extending from said seat.

4. The seating apparatus for supporting a person according to claim 3, wherein said means for supporting the abdomen region of the person include two bows which are connected to said seat and which are movable into, and out of, a position for supporting the abdomen region of the person occupying said seat.

5. The seating apparatus for supporting a person according to claim 1, wherein said convex-shaped underface of said single leg has a radius of curvature of from 25–70 cm, whereby the center of gravity of the seating apparatus and a person seated thereon generally coincides with the center of curvature of said convexed-shaped underface.

6. The seating apparatus for supporting a person according to claim 1, wherein said support for preventing said seat from overturning includes two rollers.

* * * * *